United States Patent [19]

Hayre

[11] Patent Number: 5,776,055
[45] Date of Patent: Jul. 7, 1998

[54] NONINVASIVE MEASUREMENT OF PHYSIOLOGICAL CHEMICAL IMPAIRMENT

[76] Inventor: Harb S. Hayre, 10 Legend La., Houston, Tex. 77224-9756

[21] Appl. No.: 674,143

[22] Filed: Jul. 1, 1996

[51] Int. Cl.$^6$ .................................................. A61B 5/00
[52] U.S. Cl. .................................. 600/300; 340/573
[58] Field of Search .................... 128/630, 733; 381/41, 49–50; 340/573; 379/38; 704/203, 220, 222, 230, 232, 241, 243; 395/2.09, 2.14–2.17

[56] References Cited

U.S. PATENT DOCUMENTS

| | | |
|---|---|---|
| 3,814,939 | 6/1974 | Parker et al. |
| 4,391,777 | 7/1983 | Hutson |
| 4,576,184 | 3/1986 | Westerman |
| 4,732,625 | 3/1988 | Livak |
| 4,843,377 | 6/1989 | Fuller et al. ................ 340/573 |
| 5,483,617 | 1/1996 | Patterson et al. ............ 395/2.16 |
| 5,586,171 | 12/1996 | McAllister et al. ............ 379/67 |
| 5,615,302 | 3/1997 | McEachern ................. 395/2.18 |

OTHER PUBLICATIONS

H.S. Hayre, Electronic Surveillance of Oilfield workers/Helicopter Pilots for Drug/Alcohol Use, IEEE 1986 Region 5 Conference–CH2304, pp. 26–29.

Harb. S. Hayre, Speaking of Drugs, Security Management vol.32.No. 4, Apr. 1988, pp. 98–101.

*Primary Examiner*—Francis Jaworski
*Attorney, Agent, or Firm*—Jones, Tullar & Cooper, P.C.

[57] ABSTRACT

An apparatus and method are described for detecting and measuring the physiologic response of a subject to chemical intake to determine impairment due to alcohol, inhalant, illicit drug or prescription medication. The method includes transducing a set of words spoken by the subject into electrical signals which are amplified and frequency band-limited and then Fast Fourier Transformed to obtain the frequency spectra of the speech. The ratio of speech energy in a first bandpass region with respect to energy in another bandpass region which may include the first region is computed and utilized to produce an output signal which is a measure of the subject's degree of chemical impairment.

11 Claims, 4 Drawing Sheets

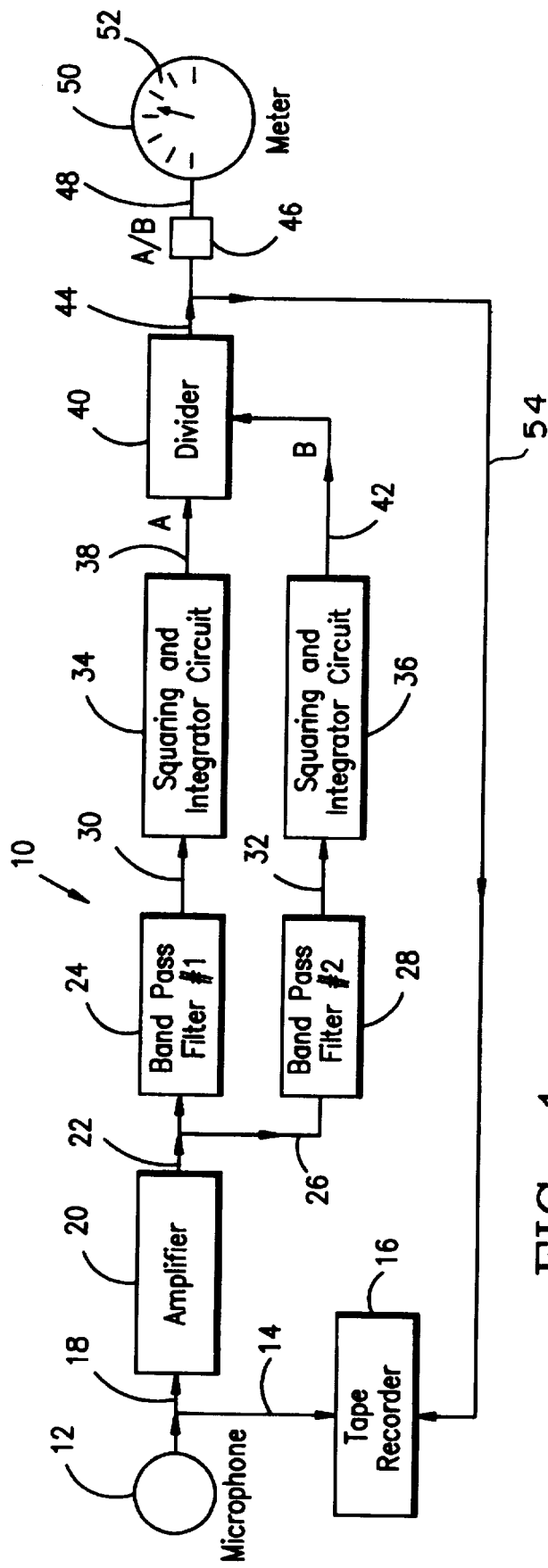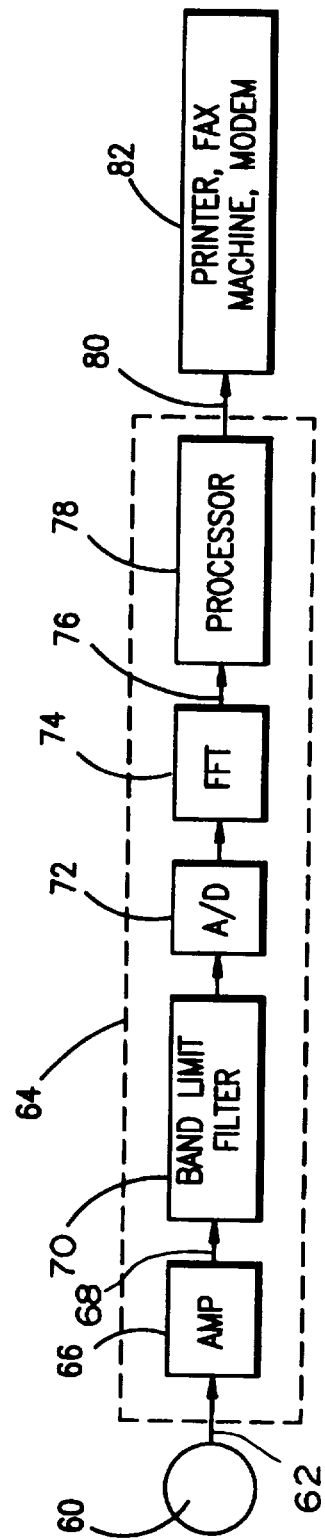
FIG. 1
FIG. 2

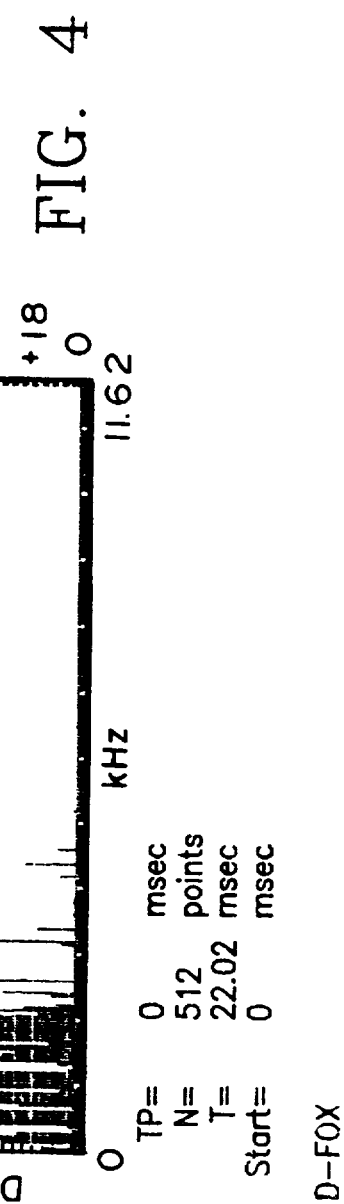

NONINVASIVE MEASUREMENT OF PHYSIOLOGICAL CHEMICAL IMPAIRMENT

BACKGROUND OF THE INVENTION

This invention relates to a noninvasive method of detecting and measuring the physiological response of a subject to chemical intake in the form of a chemical impairment measure and to an apparatus for accomplishing this method. Such chemicals include but are not limited to alcohol, illicit drugs, prescription drugs, inhalants or any combination thereof.

Over the centuries, alcohol impairment has been inferred by uncontrolled incoherency in or slurring of speech, otherwise termed as a lack of neurological/muscular coordination of human physiological systems. In recent years, various invasive methods such as blood tests, as well as urine tests of the type described in the U.S. Pat. No. 3,814,939 to Parker, et al, breath tests of the type described in the U.S. Pat. No. 4,391,777 to Hutson, hair tests, and EMG wave monitoring of the type described in the U.S. Pat. No. 4,576,184 to Westerman, have been devised to determine either blood-alcohol content (BAC) or the presence of measured nanograms/deciliter of illicit drug chemicals in a subjects' urine or blood. However, no simple, easy-to-administer, noninvasive, remotely applicable, self-normalizing and gender independent test yielding a true numerical measure of personal chemical impairment is available today.

With the advent of wide-spread use of numerous drugs and chemicals taken via mouth, nose, by injection, by smoking or any combination of these, an on-the-spot method for measuring chemical fitness (the complement of chemical impairment) for both local and remote applications is needed. Such a monitoring method is essential for determining the fitness of operators of construction equipment, boats, barges, ships, airplanes, helicopters, motor vehicles, buses, trucks, and trains, etc. for the safety of society. Moreover, monitoring for chemical fitness of office and industrial workers using sophisticated equipment and computers would significantly improve their productivity and safety in the workplace.

In automotive safety studies, the total reaction or reflex time of a driver/operator of the type described in U.S. Pat. No. 4,732,625 to Komlos is used as an indicator of driver fitness and safety. Blood-alcohol content (BAC) levels may be derived from blood tests, or a BAC estimate thereof may be obtained from breathlyzer/intoxylzer tests administered by employers and law enforcement officials. In most states, a BAC of 0.06-0.1 MG/DCL is considered to be an indication of sufficient impairment of human faculties to render an adult driver unsafe and subject to driving while intoxicated (DWI) arrest. These BAC limits are lowered to 0.0 to 0.02 levels for minors.

With the U.S. population using over 120 million tranquilizer prescriptions/year, and with rampant use and abuse of prescription drugs and alcohol on one end of the spectrum and multiple illicit drugs and/or alcohol users on the other, there exists no effective, accurate and noninvasive means to measure physiological/neurological impairment caused by chemicals. To the contrary, federal and state courts have consistently ruled that employers in fields other than transportation must establish cause for drug testing. In addition, many state laws concerning driving while intoxicated require that the driver must be impaired at the time the driver is being charged with a DWI offense by a law enforcement agency.

In many cases, numerous legal questions have also been raised about the use of urine or blood tests in both state and federal courts. Controversies arise because of the possible substitution of samples, questions about the chain of custody, operator error, violation of employee's constitutional right to privacy, or lack of cause for testing in general or for random testing. Furthermore, none of the commercially available drug tests are personalized and they might not be gender independent. All of these reasons support the need for a non-invasive test to determine chemical impairment.

SUMMARY OF THE INVENTION

An objective of the present invention is to provide a noninvasive and remotely useable apparatus and method of evaluating chemical impairment by detecting and measuring the manifestation of neurological changes reflected in human speech due to chemical intake, wherein the subject's body is neither in contact with an instrument nor subjected to any invasive testing such as being required to urinate, to give a blood sample or a hair sample, to breathe into a device, to walk a straight line, to submit to brain wave tests with electrodes attached to the head, to salivate, or the like.

Another objective of this invention is to utilize human speech as the medium by which changes in neurological states occurring in response to chemical intake are detected and measured, thus providing a unique and personalized physiological and neurological system chemical impairment measure.

A further objective is to provide an apparatus for providing a numerical measure of chemical impairment of an individual.

A further objective of the invention is to eliminate the need for a baseline or prior knowledge of the tolerance level of a subject under test, so that prior knowledge of the subject's chemical intake habits, weight, recent food intake information or the elevation above sea level of the location of the subject is not required.

The human physiological, neurological, and cerebral functions are known to automatically account for factors such as food, normal chemical intake, and the like so that any additional chemical intake induces a chemical impairment that can be measured. It has been found that a subject's speech contains personalized information about impairment due to chemicals, and that such impairment can be determined by the physiology/neurology of the subject at the time of the test.

Briefly described, the method of this invention includes the steps of transducing a set of words spoken by a subject to be tested into electrical signals which are amplified, frequency band limited, for example to 00–1160 HZ, and then Fast Fourier Transformed to obtain the frequency spectra of the speech. Preferably, the speech will be a series of short words, such as the digits 1 to 10. The ratio of energy contained in an upper frequency band; for example, 580–1160 HZ, to that contained in the entire spectrum is calculated, and the ratio multiplied by a constant. The result is then rounded off, for example to the nearest one-tenth. The resulting value represents a chemical impairment measure. Since approximately 67% of the cerebral functions and 100 muscles are involved in speech perception and generation, the chemical impairment measure described above is capable of detecting chemical impairment due to one or more chemicals consumed by a subject. This is due to the fact that such impairment produces a shift of energy toward higher frequencies in the speech spectrum, and this shift has been found to be an effective measure of chemical impairment.

In tests of the present invention, the words "one, two, eight, nine, ten," spoken by twenty persons arrested for DWI by a police department were tape-recorded, as were the words of thousands of others under the influence of various illicit and prescription drugs. These spoken words were analyzed in the manner to be described in order to determine the impairment measure of the subjects under test. The level of impairment was later verified using BAC data, and other data on reaction time and chemical intake. Every DWI subject who was found to be impaired was found to have an impairment measure of above 2.0, as determined by using the method and apparatus of this invention.

It was also discovered during these tests that persons with the same BAC level had widely different chemical impairment measures, as was logically expected since no two persons have identical physiologies, chemical tolerances or exactly the same responses to the same chemical intake, but this had not previously been quantitatively verified. It was reported in the U.S. National Institute of Alcohol Abuse and Alcoholism Alcohol Alert (Number 25 PH 351 of July, 1994), that "the degree of impairment associated with a given BAC is not constant and may vary among individuals."

BRIEF DESCRIPTION OF THE DRAWINGS

The foregoing as well as additional objects, features, and advantages of the present invention will be understood by those of skill in the art from a consideration of the following detailed description of preferred embodiments thereof, taken with the accompanying drawings, in which:

FIG. 1 is a block diagram of a chemical impairment analog measurement apparatus in accordance with the present invention;

FIG. 2 is a block diagram of an analog and digital (hybrid) chemical impairment measurement apparatus in accordance with the present invention;

FIG. 3 is a time domain representation of an 11.6 kilohertz (kHz) bandwidth limited speech signal;

FIG. 4 is a frequency spectral density of the speech signal shown in FIG. 3 in decibels (db) vs frequency in Hertz (Hz);

DETAILED DESCRIPTION OF PREFERRED EMBODIMENTS

Figure 5:
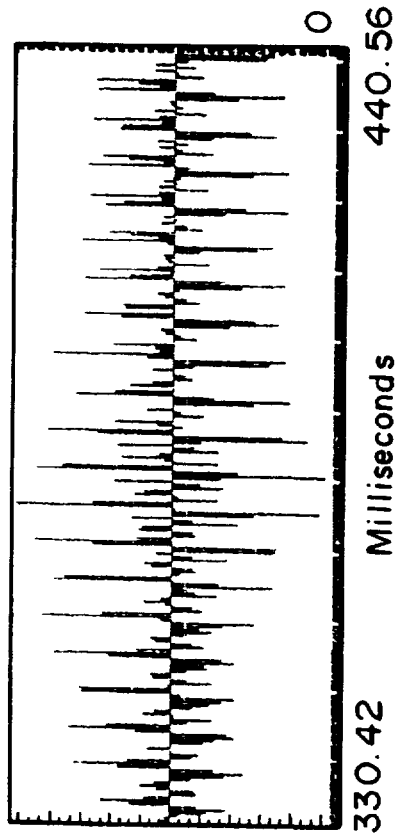
FIG. 5 is a time domain representation of the 1.16 kHz band limited speech signal of FIG. 3.

Turning now to a more detailed description of the present invention, there is illustrated in FIG. 1 a preferred form of an analog chemical impairment measurement apparatus generally indicated at 10. The apparatus 10 includes a commercially available hand-held microphone 12, the output of which is connected by way of line 14 to a commercially available cassette tape recorder 16. If desired, the microphone 12 may be built into the tape recorder, as is conventional in available cassette tape recorders. The output of the microphone is also supplied by way of line 18 to a suitable audio frequency amplifier 20 such as a model AD620, available from Analog Devices, Inc.

Although the microphone is illustrated as a cassette tape recorder microphone, it will be understood that any similar transducer such as a radio-telephone, cellular telephone, or standard telephone can be used to supply voice signals to the recorder 16 and the amplifier 20, in which case the connections between the microphone and these units would be by telephone line or radio signals instead of the indicated wire connections.

The voice signal received by amplifier 20 is amplified, for example by a gain of 10, with the output being supplied by way of line 22 to a bandpass filter 24 and by way line 26 to a parallel band pass filter 28. These filters may be commercially available bandpass filters such as model 713H4B and model 70612B, available from Frequency Devices, Inc. Filter 24 is selected to have a bandwidth of, for example, 0–1160 Hz, while filter 28 has a bandwidth of, for example, 580–1160 Hz, 580 Hz being the mid-frequency of the 0–1160 Hz spectrum.

The voice signals produced by microphone 12 are exemplified by the waveform illustrated in FIG. 3. After amplification and filtering in bandpass filter 24, the waveform of FIG. 3 is converted to the waveform of FIG. 5.

The analog output signals appearing on output lines 30 and 32 of filters 24 and 28, respectively, are squared and integrated in corresponding squaring and integrating circuits 34 and 36, respectively, over a period of 0.2 seconds. These are commercially available squaring and integrating circuits such as model OP275 available from Analog Devices, Inc. The integrated output from circuit 34 appears on line 38 and is supplied to one input of a divider 40. The output from circuit 36 is supplied by way of line 42 to a second input of divider 40 so that the integrated output from filter 28 is divided by the integrated output from filter 24 in a commercially available divider circuit 40 such as model OP275, available from Analog Devices, Inc.

The signal on line 38 may be represented by "A" and the signal on line 42 may be represented by "B", with the resulting output from divider 40 appearing on output line 44 as the ratio B/A. This signal may be supplied through a suitable amplifier 46 which multiplies the value B/A by a constant K, such as 10, and the resulting signal is supplied by way of line 48 to a suitable analog meter 50. This meter incorporates a suitable scale 52, such as a scale of 0–10, to provide an immediate chemical impairment measure.

The analog output of the divider 40 on line 44 may also be supplied by way of line 54 to the tape recorder 16 for later use.

Another embodiment of the invention is illustrated in FIG. 2, which is a block diagram of a combined analog and digital measurement apparatus. In this embodiment, a microphone 60, such as a Radio Shack model 33-985, or a digital microphone such as that provided by Analog Devices, Inc., or the equivalent is used to transduce spoken words into their corresponding electrical signals which are supplied by way of line 62 to suitable signal processing equipment generally indicated at 64. Such equipment may be a commercially available personal computer such as a 386DX30 or equivalent, including suitable audio processing boards.

Figure 6:
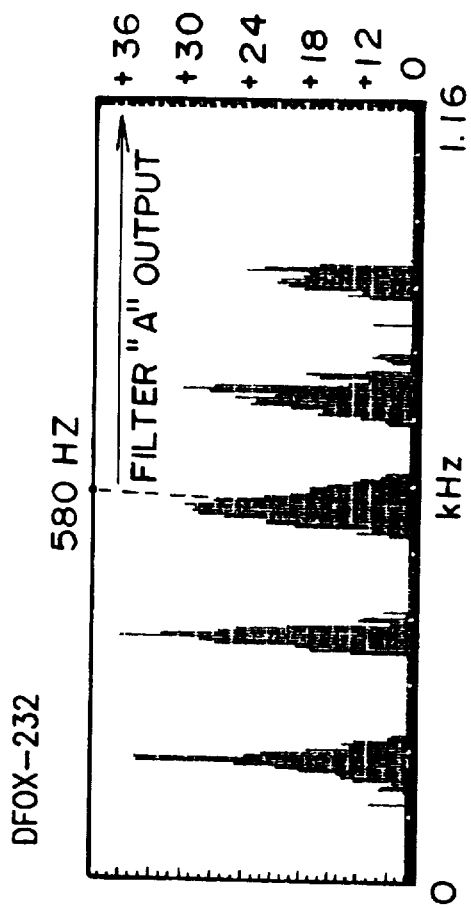
FIG. 6 is a diagram illustrating the frequency spectral density of the speech signal shown in FIG. 5.

The computer 64 preferably includes an amplifier 66 for receiving audio signals on line 62, with the amplified signals being applied by way of line 68 to a band pass filter 70. Such a filter may be an antialiasing filter such as "Tahiti" model personal computer board available from Turtle Beach Systems, Inc. which filters and digitizes the audio signals as indicated by the analog to digital circuit 72 in FIG. 2. The digitized signals are then Fast Fourier Transformed (FFT) as indicated at FFT block 74, and the resulting signal is processed in processor 78 of computer 64 utilizing commercially available digital signal processing software, such as "Spectra Plus 3.0," available from Pioneer Hill Software, Inc., to produce power spectral density signals P(f) on output line 80. The power spectral density signals thus obtained are shown in FIGS. 4 and 6.

The basic equation for determining the power spectral density is as follows:

$$S(f_k) = \left[ (1/N) \sum_{n=0}^{N-1} x(t_n)\exp(-jw_k t_n) \right]^2 \quad \text{(Eq. 1)}$$

where $S(f_k)$=power spectral density
$W_k=kW_0=2\pi f_o k$
$t_n$=Time location of $n^{th}$ sample
$T_o$=Sampling period=

$$\frac{1}{f_o}$$

N=Total number of samples

The function $x(t_n=nT_0)$ is an n-point sequence that is T seconds in length of digitized speech. When this is Discrete Fourier Transformed, the function becomes:

$$x(f_k) = 1/N \sum_{n=0}^{N-1} x(nT_0)\exp(-j2\pi k n/N) \quad \text{(Eq. 2)}$$

and its power spectral density is defined as:

$$S(f_k)=|x(f_k)|^2 \quad \text{(Eq. 3)}$$

The power spectral density S(fk) is converted into decibels (db), and is processed in the processor 78 in accordance with the following equation to yield the chemical impairment measure CIM of the present invention:

$$CIM = K \left[ \sum_{f=580}^{f=1160} S_d(f) / \sum_{f=00}^{f=1160} S_d(f) \right] \quad \text{(Eq. 4)}$$

where K is a constant multiplier such as ten, resulting in values of the chemical impairment measure ranging from zero to ten.

The value of the chemical impairment measure is supplied by way of line 80 to a display or storage unit 82 such as a printer, a FAX machine, a modem, or the like which allows the value to be displayed, printed or stored for future use, or sent to a remote location over a communication link. For example, the computer 64 may incorporate a FAX modem which will transmit the chemical impairment measure to a remote computer or FAX machine by way of any commercially available communication link.

Figure 7:
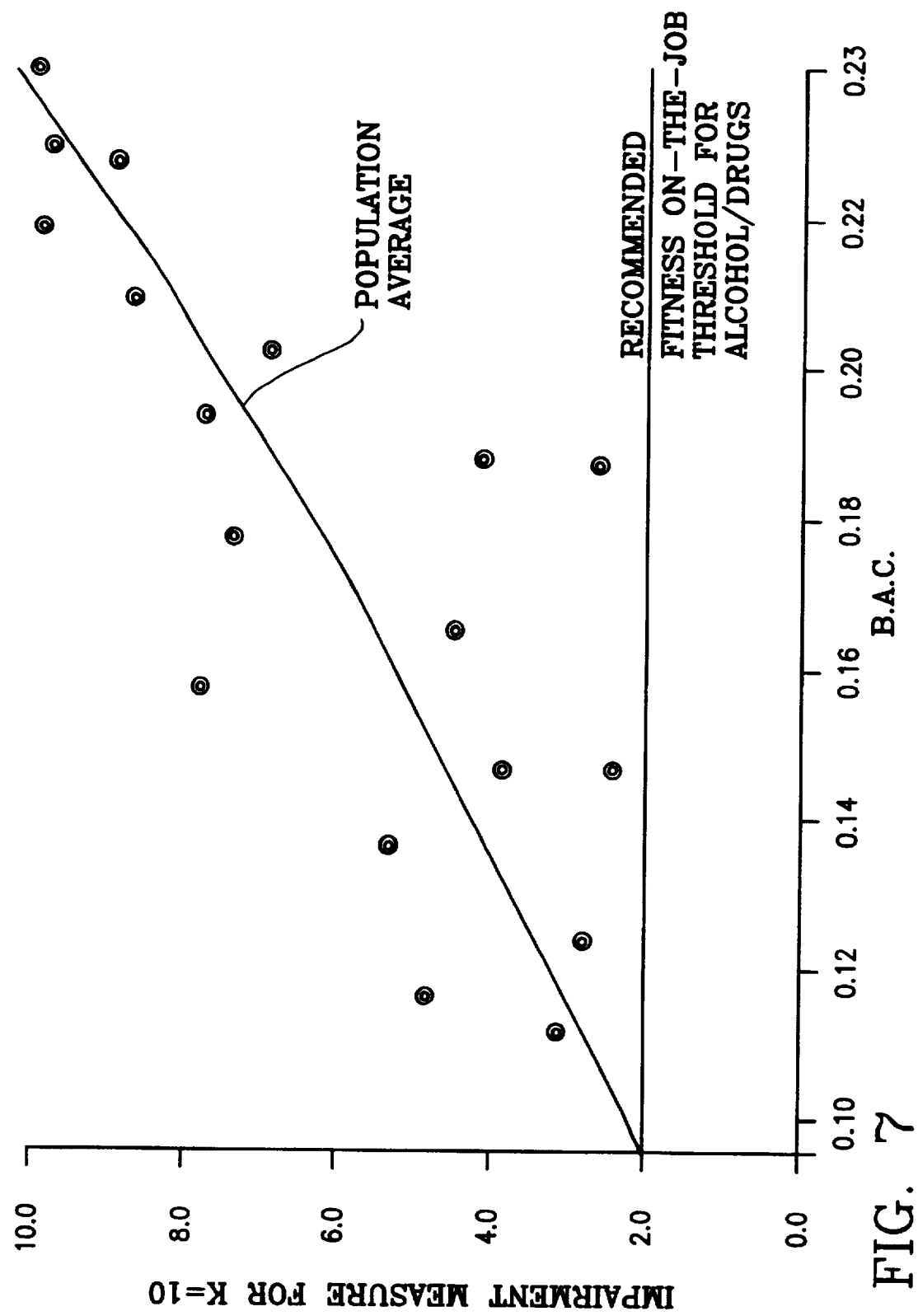
FIG. 7 is a graph illustrating chemical impairment measure versus blood alcohol content (BAC) for twenty driving-while-intoxicated (DWI) subjects for K=10.

The measurement and determination of the chemical impairment of the present invention provides an accurate measurement of alcohol impairment, as illustrated by the graph of FIG. 7, in which chemical impairment measurements are compared to actual blood alcohol content measurements for 20 subjects. The procedure carried out in accordance with the invention is a truly noninvasive procedure and permits determination of the physiological and neurological manifestations of chemical impairment. The apparatus of the invention provides a quantitative measure of such impairment, and does not required a baseline measurement for use as a reference level in making the required calculations for a given individual. Further, the present invention responds to physiological manifestations produced by one or more chemicals consumed by the subject in any manner. The process relies on the subject's chemically impaired neurological system, a large portion of which is used to generate speech. The process is independent of the subject's ethnic background, regional accent, pronunciation of words, physiological disorders, or psychological stress. It is not necessary to have speech processing equipment at the location where the subject is being tested, since the subject's speech can be transmitted from a remote location by any communication link to centrally located equipment embodying the apparatus of the present invention.

While certain advantageous embodiments have been chosen to illustrate the invention, those skilled in the art will understand that various changes and modifications can be made in implementing the objectives of the invention, and accordingly the true spirit and scope of the invention is limited only by the following claims:

What is claimed is:

1. A noninvasive method for identifying and measuring the physiological manifestations of chemical impairment in a human subject, comprising:

converting the subject's spoken words into a corresponding electrical signals;

amplifying the said electrical signals;

frequency band limiting the said electrical signals to produce corresponding conditioned electrical signals;

determining the frequency spectral density of the conditioned speech signals;

determining a first value corresponding to the energy contained in the said upper half frequency band of signal spectral density from 580 to 1160 Hertz;

determining a second value corresponding to the energy contained in the entire frequency band of the said signal spectral density from 00 to 1160 Hertz; and determining the ratio of the said first value to the said second value to obtain a third value corresponding to the said chemical impairment.

2. The method of claim 1, further including rounding the said third value to two digits and multiplying it by a constant value K, to obtain a numerical chemical impairment measure.

3. The method of claim 2, further including compressing the range of the chemical impairment measure by selecting a narrow bandwidth of said electrical signals.

4. The method of claim 2, further including converting the subject's words to electric signals at a first location and transmitting the signals to a remote location for the remaining steps of the method.

5. The method of claim 2, further including comparing said numerical chemical impairment measure with the measured blood-alcohol content values to provide an equivalent chemical impairment measure.

6. The method of claim 2, wherein determining the ratio of said first and second values accounts for a subject's chemical tolerance level, food ingested prior to test, and elevation of the location of the test site.

7. The method of claim 2, further including offering an individualized impairment measure for each of a plurality of subjects.

8. Apparatus for noninvasive identification and measurement of physiological manifestations of chemical impairment in a human subject, comprising:

means responsive to the speech of a subject to convert the speech into corresponding electrical signals;

an amplifier for amplifying said signals, first and second band pass filters having inputs connected in parallel to receive said amplified signals;

first and second integrator circuits connected to said first and second band pass filters, respectively, to produce first and second band pass limited and integrated speech signals; and a divider circuit having first and second inputs and an output, said first input being connected to said first integrator circuit to receive said first integrated speech signal and said second input being connected to said second integrator circuit to receive said second integrated speech signal, said first integrated speech signal being divided by said second integrated speech signal in said divider to produce an output signal which is a measure of chemical impairment in the subject's speech.

9. The apparatus of claim 8, further including a display responsive to said output signal.

10. The apparatus of claim 8, further including a recorder for recording said output signal.

11. Apparatus for noninvasive identification and measurement of physiological manifestations of chemical impairment of a subject, comprising:

an amplifier;

means responsive to the speech of a subject to convert the speech into corresponding electrical speech signals;

a band limit filter;

means supplying said signals through said amplifier to said band limit filter to produce band-limited signals;

an analog-to-digital converter for converting said band-limited signals to digital signals;

means for Fast Fourier Transforming said digital signals and producing a power spectrum corresponding to said speech signals; and means for integrating portions of said power spectrum and obtaining a ratio of said integrated portions to provide a measure of chemical impairment of the subject.

* * * * *